United States Patent
Wu et al.

(10) Patent No.: US 12,403,443 B2
(45) Date of Patent: Sep. 2, 2025

(54) HYBRID MICROCAPSULES

(71) Applicant: FIRMENICH SA, Satigny (CH)

(72) Inventors: Yongtao Wu, Shanghai (CN); Jia-Jun Shen, Shanghai (CN)

(73) Assignee: FIRMENICH SA, Satigny (CH)

( * ) Notice: Subject to any disclaimer, the term of this patent is extended or adjusted under 35 U.S.C. 154(b) by 699 days.

(21) Appl. No.: 17/757,274

(22) PCT Filed: Dec. 10, 2020

(86) PCT No.: PCT/EP2020/085575
§ 371 (c)(1),
(2) Date: Jun. 13, 2022

(87) PCT Pub. No.: WO2021/116306
PCT Pub. Date: Jun. 17, 2021

(65) Prior Publication Data
US 2023/0001373 A1    Jan. 5, 2023

(30) Foreign Application Priority Data

Dec. 13, 2019 (WO) ................ PCT/CN2019/124983
Feb. 11, 2020 (EP) ................. 20156639.5

(51) Int. Cl.
| B01J 13/16 | (2006.01) |
| A61K 8/11 | (2006.01) |
| A61K 8/73 | (2006.01) |
| A61Q 13/00 | (2006.01) |
| C11D 3/50 | (2006.01) |

(52) U.S. Cl.
CPC ............. B01J 13/16 (2013.01); A61K 8/11 (2013.01); A61K 8/736 (2013.01); A61Q 13/00 (2013.01); C11D 3/505 (2013.01); *A61K 2800/56* (2013.01)

(58) Field of Classification Search
CPC .... A61K 8/11; A61K 8/736; A61K 2800/412; A61K 2800/56; B01J 13/16; B01J 13/14; A61Q 13/00; A61Q 5/02; A61Q 5/12; A01N 25/28; C11D 3/505
USPC ....................................... 512/4, 1
See application file for complete search history.

(56) References Cited

U.S. PATENT DOCUMENTS

2006/0188578 A1 * 8/2006 Fernandez ........... A61K 9/5161
977/906

FOREIGN PATENT DOCUMENTS

| WO | WO-2014130204 A1 * | 8/2014 | ............... A61K 8/06 |
| WO | 2019063515 A1 | 4/2019 | |
| WO | 2019179939 A1 | 9/2019 | |

OTHER PUBLICATIONS

Nan Fangfang et al, "Preparation of uniform-sized colloidosomes based on chitosan-coated alginate particles and its application for oral insulin delivery", Sep. 4, 2014 (Sep. 4, 2014), pp. 7403-7409, vol. 2, No. 42, GB.
Bago Rodriguez Ana Maria et al., "Capsules from Pickering emulsion templates", Oct. 15, 2019 (Oct. 15, 2019), pp. 107-129, vol. 44.
International Search Report and Written Opinion for corresponding PCT/EP2020/085575 mailed Feb. 15, 2021; 15 pages.
Wei et al., "Chitosan nanoparticles as particular emulsifier for preparation of novel pH-responsive Pickering emulsions and PLGA microcapsules", Polymer, 2012, pp. 1229-1235, 53(6).
Ding et al., "Preparation of Functional Patterned Protein Arrays via the Combination of Inverse Emulsion and Breath Figure Method", Chemical Journal of Chinese Universities, 2018, pp. 1311-1318, 39(6).
Mwangi et al., "Facile method for forming ionically cross-linked chitosan microcapsules from Pickering emulsion templates", Food Hydrocolloids, 2016, pp. 26-33, 55.
Yang et al., "Core-shell chitosan microcapsules for programmed sequential drug release", ACS Applied Materials & Interfaces, 2016, pp. 10524-10534, 8(16).

* cited by examiner

*Primary Examiner* — Jessica Whiteley
(74) *Attorney, Agent, or Firm* — Armstrong Teasdale LLP

(57) ABSTRACT

Described herein are hybrid microcapsules with a hydrophobic material-based core, such as a perfume, and a polymeric shell including chitosan particles. Processes for preparing such microcapsules are also described, as are perfuming compositions and consumer products including the capsules, in particular, perfumed consumer products in the form of home care or personal care products.

19 Claims, 1 Drawing Sheet

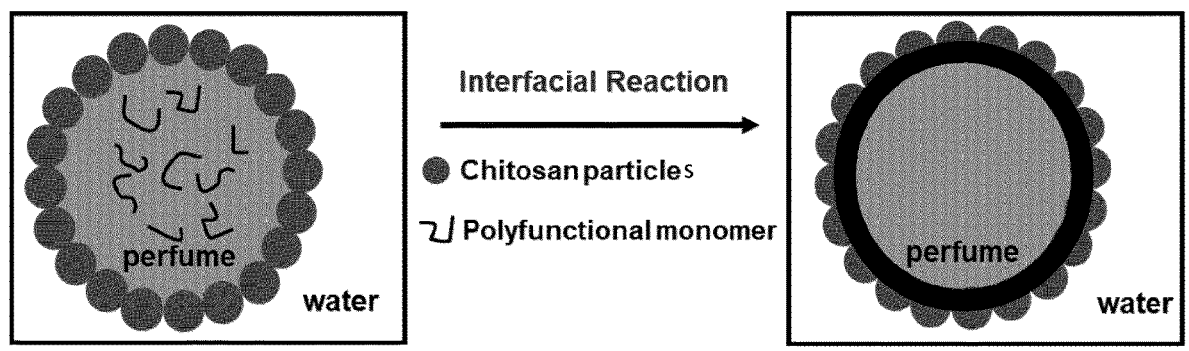

HYBRID MICROCAPSULES

CROSS-REFERENCE TO RELATED APPLICATIONS

This application is a U.S. National Phase Application of International Patent Application No. PCT/EP2020/085575, filed Dec. 10, 2020, whichclaims priority to European Patent Application No. 20156639.5, filed Feb. 11, 2020, and to Chinese (International) Patent Application No. PCT/CN2019/124983, filed Dec. 13, 2019, each of which is hereby incorporated by reference herein in its entirety.

TECHNICAL FIELD

The present invention relates to hybrid microcapsules, with a hydrophobic material-based core, preferably a perfume, and a polymeric shell comprising chitosan particles. Process for preparing said microcapsules is also an object of the invention. Perfuming compositions and consumer products comprising said capsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume, are needed to protect and later release the core payload when triggered. A key requirement from the industry regarding these systems is to survive suspension in challenging bases without physically dissociating or degrading. For instance, fragranced personal and household cleansers containing high levels of aggressive surfactant detergents are very challenging for the stability of microcapsules.

Aminoplast microcapsules formed of a melamine-formaldehyde resin have been largely used to encapsulate hydrophobic actives, thus protecting said actives and providing their controlled release. However, capsules such as aminoplast ones suffer from stability problems when used in consumer products comprising surfactants, such as perfumery consumer products, especially after prolonged storage at elevated temperatures. In such products, even though the capsule wall remains intact, the encapsulated active tends to leak out of the capsule by diffusion through the wall due to the presence of surfactants that are able to solubilise the encapsulated active in the product base. The leakage phenomenon reduces the efficiency of the capsules to protect the active and provide its controlled release.

A variety of strategies have been described to improve the stability of oil core-based microcapsules. Cross-linking of capsule walls, with chemical groups such as poly(amines) and poly(isocyanates), has been described as a way to improve stability of microcapsules. WO2011/154893 discloses for instance a process for the preparation of polyurea microcapsules using a combination of aromatic and aliphatic polyisocyanates in specific relative concentrations.

Stabilization of oil/water interfaces with inorganic particles has been described in so-called Pickering emulsions. In this context, functionalization of inorganic particles to allow their cross-linking is known. For instance, Pickering emulsions cross-linked from an outer water phase with polyelectrolytes providing electrostatic interactions have been the object of prior disclosures (Li Jian et al. in Langmuir (2010), 26(19), 15554-15560). However, such systems are very likely to dissociate in a surfactant base or in ethanol over time as electrostatic interactions are insufficient to promote stability. Covalent cross-linking has also been described in relation with Pickering emulsion in the preparation of colloidosomes. In particular, the use of diisocyanates as cross-linker has been disclosed in scientific publications. WO2009/063257 also describes the use of polyisocyanates as possible cross-linker for surface-modified inorganic particles in order to prepare microcapsules with increased level of protection from UV light for the contents. These products are typically intended for agrochemical applications. This type of system is not suitable for perfume encapsulation. In fact, in order to maintain a good morphology and permeability of the microcapsules, an excess of surface-modified inorganic particles is needed. Another problem is that these microcapsules show little margin for size adjustment. Furthermore, the amount of adsorbed particles at the oil-water interface is limited which affects the properties of the capsule membranes.

Therefore, there is still a need to provide new microcapsules while not compromising on their performance, in particular in terms of stability in a consumer product, as well as in delivering a good performance in terms of hydrophobic material delivery.

SUMMARY OF THE INVENTION

A first aspect of the invention is therefore a core-shell microcapsule comprising:
  a) an oil-based core comprising a hydrophobic material, preferably a perfume oil; and
  b) a polymeric shell comprising chitosan particles.

In a second aspect of the invention is a core-shell microcapsule slurry comprising at least a microcapsule made of:
  a) an oil-based core comprising a hydrophobic material, preferably a perfume oil; and
  b) a polymeric shell comprising chitosan particles.

A third aspect of the invention is a process for preparing core-shell microcapsules or core-shell microcapsule slurry as defined above, wherein the process comprises the steps of:
  1) suspending in water chitosan particles to form a water phase;
  2) preparing an oil phase comprising a hydrophobic material, preferably a perfume oil;
  3) adding the oil phase to the water phase and mixing them to form an oil-in-water Pickering emulsion, under conditions allowing the formation of core-shell microcapsule by interfacial polymerization and/or interfacial reaction, wherein a polyfunctional monomer is added in step 1) in the water phase and/or in step 2) in the oil phase.

In a fourth aspect, the invention concerns a microcapsule obtainable by such a process as well as perfuming compositions and consumer products containing them.

In a last aspect, the invention relates to the use of chitosan based particles, for the stabilization of a Pickering emulsion further subjected to an interfacial polymerisation reaction.

BRIEF DESCRIPTION OF THE FIGURES

FIG. 1: is a schematic representation of the formation of a Pickering emulsion when chitosan particles are used to stabilize the oil phase.

DETAILED DESCRIPTION OF THE INVENTION

Unless stated otherwise, percentages (%) are meant to designate percent by weight of a composition.

By "active ingredient", it is meant a single compound or a combination of ingredients.

By "perfume or flavor oil", it is meant a single perfuming or flavoring compound or a mixture of several perfuming or flavoring compounds.

By "consumer product" or "end-product" it is meant a manufactured product ready to be distributed, sold and used by a consumer.

A "microcapsule", or the similar, in the present invention has a morphology that can vary from a core-shell to a matrix type. According to one embodiment, it is of the core-shell type. In this case, the microcapsules comprise a core based on a hydrophobic material, typically a perfume, and a shell comprising chitosan particles.

Microcapsules have a particle size distribution in the micron range (e.g. a mean diameter) comprised between about 1 and 3000 microns, preferably comprised between 1 and 1000 microns, more preferably between 1 and 500 microns, and even more preferably between 5 and 50 microns. The polymeric shell of the microcapsule according to the present invention is formed by interfacial polymerization and/or interfacial reaction in the presence of chitosan particles.

By "particle size" it is meant an average diameter of particles based on size distribution measured by dynamic light scattering (DLS) using Zetasizer Nano ZS equipment from Malvern Instruments Ltd., UK when particles are dispersed into a water phase.

By "microcapsules size" it is meant the volume mean diameter (D[4,3]) of the relevant capsules, capsules suspension as obtained by laser light scattering of a diluted sample in a Malvern Mastersizer 3000.

By "polyfunctional monomer", it is meant a molecule that, as unit, reacts or binds chemically to form a polymer or a supramolecular polymer. The polyfunctional monomer is oil soluble or water soluble. The polyfunctional monomer of the invention has at least two functional groups that are capable to react with or bind to functional groups of another component (for example chitosan particles) and/or capable to polymerize to form a polymeric shell. The wording "shell" and "wall" are used indifferently in the present invention.

By "polyurea-based" wall or shell, it is meant that the polymeric shell comprises urea linkages produced by either an amino-functional crosslinker or hydrolysis of isocyanate groups to produce amino groups capable of further reacting with isocyanate groups during interfacial polymerization.

It has now surprisingly been found that performing core-shell microcapsules encapsulating hydrophobic material could be obtained when chitosan particles are comprised within the shell. The microcapsules of the invention therefore provides a solution to the above-mentioned problems as it improves the storage stability in challenging bases even with a low concentration of polymeric material in the shell and it improves the performance in application owing to the cationic surface charges of microcapsules from the chitosan particles.

Core-Shell Microcapsule

A first object of the invention is a core-shell microcapsule comprising:

a) an oil-based core comprising a hydrophobic material, preferably a perfume oil; and b) a polymeric shell comprising chitosan particles.

Hydrophobic Material

The hydrophobic material according to the invention can be "inert" material like solvents or active ingredients.

When hydrophobic materials are active ingredients, they are preferably chosen from the group consisting of flavors, flavor ingredients, perfumes, perfume ingredients, nutraceuticals, cosmetics, pest control agents, biocide actives and mixtures thereof.

According to a particular embodiment, the hydrophobic material comprises a mixture of a perfume with another ingredient selected from the group consisting of nutraceuticals, cosmetics, pest control agents and biocide actives.

According to a particular embodiment, the hydrophobic material comprises a mixture of biocide actives with another ingredient selected from the group consisting of perfumes, nutraceuticals, cosmetics, pest control agents.

According to a particular embodiment, the hydrophobic material comprises a mixture of pest control agents with another ingredient selected from the group consisting of perfumes, nutraceuticals, cosmetics, biocide actives.

According to a particular embodiment, the hydrophobic material comprises a perfume.

According to a particular embodiment, the hydrophobic material consists of a perfume.

According to a particular embodiment, the hydrophobic material consists of biocide actives.

According to a particular embodiment, the hydrophobic material consists of pest control agents.

By "perfume" (or also "perfume oil") what is meant here is an ingredient or a composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odor. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes a combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lastingness, blooming, malodor counteraction, antimicrobial effect, microbial stability, pest control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery.

In particular one may cite perfuming ingredients which are commonly used in perfume formulations, such as:

Aldehydic ingredients: decanal, dodecanal, 2-methyl-undecanal, 10-undecenal, octanal, nonanal and/or nonenal;

Aromatic-herbal ingredients: *eucalyptus* oil, camphor, eucalyptol, 5-methyltricyclo[6.2.1.0~2,7~]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2- acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{(1S)-1-[(1R)-3,3-dimethylcyclohexyl] ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclohexyl)ethoxycarbonyl]methyl propanoate;

Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R, E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

It is also understood that said ingredients may also be compounds known to release in a controlled manner various types of perfuming compounds also known as properfume or profragrance. Non-limiting examples of suitable properfumes may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate, 3,7-dimethylocta-2,6-dien-1-yl oxo(phenyl)acetate, (Z)-hex-3-en-1-yl oxo(phenyl)acetate, 3,7-dimethyl-2,6-octadien-1-yl hexadecanoate, bis(3,7-dimethylocta-2,6-dien-1-yl) succinate, (2-((2-methylundec-1-en-1-yl)oxy)ethyl)benzene, 1-methoxy-4-(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl) naphthalene, (2-phenethoxyvinyl)benzene, 2-(1-((3,7-dimethyloct-6-en-1-yl)oxy)prop-1-en-2-yl)naphthalene or a mixture thereof.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Preferred perfuming ingredients are those having a high steric hindrance and in particular those from one of the following groups:

Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one $C_7$ to $C_{20}$ ring structure;

Group 7: perfuming ingredients having a log P value above 3.5 and comprising at least one tert-butyl or at least one trichloromethyl substitutent; Examples of ingredients from each of these groups are:

Group 1: 2,4-dimethyl-3-cyclohexene-1-carbaldehyde (origin: Firmenich SA, Geneva, Switzerland), isocyclocitral, menthone, isomenthone, methyl 2,2-dimethyl-6-methylene-1-cyclohexanecarboxylate (origin: Firmenich SA, Geneva, Switzerland), nerone, terpineol, dihydroterpineol, terpenyl acetate, dihydroterpenyl acetate, dipentene, eucalyptol, hexylate, rose oxide, (S)-1,8-p-menthadiene-7-ol (origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, tetrahydro-4-methyl-2-phenyl-2H-pyran (origin: Firmenich SA, Geneva, Switzerland), cyclohexyl acetate, cyclanol acetate, 1,4-cyclohexane diethyldicarboxylate (origin: Firmenich SA, Geneva, Switzerland), (3ARS,6SR,7ASR)-perhydro-3,6-dimethyl-benzo[B]furan-2-one (origin: Firmenich SA, Geneva, Switzerland), ((6R)-perhydro-3,6-dimethyl-benzo[B]furan-2-one (origin: Firmenich SA, Geneva, Switzerland), 2,4,6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yl)-2-buten-1-ol (origin: Firmenich SA, Geneva, Switzerland), (1'R,E)-3,3-dimethyl-5-(2',2',3'-trimethyl-3'-cyclopenten-1'-yl)-4-penten-2-ol (origin: Firmenich SA, Geneva, Switzerland), 2-heptylcyclopentanone, methyl-cis-3-oxo-2-pentyl-1-cyclopentane acetate (origin: Firmenich SA, Geneva, Switzerland), 2,2,5-Trimethyl-5-pentyl-1-cyclopentanone (origin: Firmenich SA, Geneva, Switzerland), 3,3-dimethyl-5-(2,2,3-trimethyl-3-cyclopenten-1-yl)-4-penten-2-ol (origin: Firmenich SA, Geneva, Switzerland), 3-methyl-5-(2,2,3-trimethyl-3-cyclopenten-1-yl)-2-pentanol (origin, Givaudan SA, Vernier, Switzerland);

Group 3: damascones, 1-(5,5-dimethyl-1-cyclohexen-1-yl)-4-penten-1-one (origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, mixture of 1-(5,5-dimethyl-1-cyclohexen-1-yl)-4-penten-1-one and 1-(3,3-dimethyl-1-cyclohexen-1-yl)-4-penten-1-one (origin: Firmenich SA, Geneva, Switzerland), 1-(2,6,6-trimethyl-1-cyclohexen-1-yl)-2-buten-1-one (origin: Firmenich SA, Geneva, Switzerland), (1S,1'R)-[1-(3',3'-Dimethyl-1'-cyclohexyl)ethoxycarbonyl]methyl propanoate (origin: Firmenich SA, Geneva, Switzerland), 2-tert-butyl-1-cyclohexyl acetate (origin: International Flavors and Fragrances, USA), 1-(2,2,3,6-tetramethyl-cyclohexyl)-3-hexanol (origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, 4-(1,1-dimethylethyl)-1-cyclohexyl acetate (origin: Firmenich SA, Geneva, Switzerland), 8-methoxy-1-p-menthene, (1S,1'R)-2-[1-(3',3'-dimethyl-1'-cyclohexyl)ethoxy]-2-methylpropyl propanoate (origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), a mixture of (1RS,2SR,6RS,7RS,8SR)-tricyclo[5.2.1.0-2,6-]dec-3-en-8-yl 2-methylpropanoate and (1RS,2SR,6RS,7RS,8SR)-tricyclo[5.2.1.0-2,6-]dec-4-en-8-yl 2-methylpropanoate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), a mixture of 3-(3,3-dimethyl-5-indanyl)propanal and 3-(1,1-dimethyl-5-indanyl)propanal (origin: Firmenich SA, Geneva, Switzerland), 3',4-dimethyl-tricyclo[6.2.1.0(2,7)]undec-4-ene-9-spiro-2'-oxirane (origin: Firmenich SA, Geneva, Switzerland), 9/10-ethyldiene-3-oxatricyclo[6.2.1.0(2,7)]undecane, (perhydro-5,5,8A-trimethyl-2-naphthalenyl acetate (origin: Firmenich SA, Geneva, Switzerland), octalynol, (dodecahydro-3a,6,6,9a-tetramethyl-naphtho[2,1-b]furan, origin: Firmenich SA, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, pinene, camphene, 8-methoxycedrane, (8-methoxy-2,6,6,8-tetramethyl-tricyclo[5.3.1.0(1,5)]undecane (origin: Firmenich SA, Geneva, Switzerland), cedrene, cedrenol, cedrol, mixture of 9-ethylidene-3-oxatricyclo[6.2.1.0(2,7)]undecan-4-one and 10-ethylidene-3-oxatricyclo[6.2.1.0(2,7)]undecan-4-one (origin: Firmenich SA, Geneva, Switzerland), 3-methoxy-7,7-dimethyl-10-methylene-bicyclo[4.3.1]decane (origin: Firmenich SA, Geneva, Switzerland);

Group 6: (trimethyl-13-oxabicyclo-[10.1.0]-trideca-4,8-diene (origin: Firmenich SA, Geneva, Switzerland), Ambrettolide LG ((E)-9-hexadecen-16-olide, origin: Firmenich SA, Geneva, Switzerland), pentadecenolide (origin: Firmenich SA, Geneva, Switzerland), muscenone (3-methyl-(4/5)-cyclopentadecenone, origin: Firmenich SA, Geneva, Switzerland), 3-methylcyclopentadecanone (origin: Firmenich SA, Geneva, Switzerland), pentadecanolide (origin: Firmenich SA, Geneva, Switzerland), cyclopentadecanone (origin: Firmenich SA, Geneva, Switzerland), 1-ethoxyethoxy) cyclododecane (origin: Firmenich SA, Geneva, Switzerland), 1,4-dioxacycloheptadecane-5,17-dione, 4,8-cyclododecadien-1-one;

Group 7: (+−)-2-methyl-3-[4-(2-methyl-2-propanyl)phenyl]propanal (origin: Givaudan SA, Vernier, Switzerland), 2,2,2-trichloro-1-phenylethyl acetate.

Preferably, the perfume comprises at least 30%, preferably at least 50%, more preferably at least 60% of ingredients selected from Groups 1 to 7, as defined above. More preferably said perfume comprises at least 30%, preferably at least 50% of ingredients from Groups 3 to 7, as defined above. Most preferably said perfume comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a log P above 3, preferably above 3.5 and even more preferably above 3.75.

Preferably, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols.

According to an embodiment, the oil phase (or the oil-based core) comprises:
  25-100 wt % of a perfume oil comprising at least 15 wt % of high impact perfume raw materials having a Log T<−4, and
  0-75 wt % of a density balancing material having a density greater than 1.07 $g/cm^3$.

The nature of high impact perfume raw materials having a Log T<−4 and density balancing material having a density greater than 1.07 $g/cm^3$ are described in WO2018115250, the content of which are included by reference.

The term "biocide" refers to a chemical substance capable of killing living organisms (e.g. microorganisms) or reducing or preventing their growth and/or accumulation. Biocides are commonly used in medicine, agriculture, forestry, and in industry where they prevent the fouling of, for example, water, agricultural products including seed, and oil pipelines. A biocide can be a pesticide, including a fungicide, herbicide, insecticide, algicide, molluscicide, miticide and rodenticide; and/or an antimicrobial such as a germicide, antibiotic, antibacterial, antiviral, antifungal, antiprotozoal and/or antiparasite.

As used herein, a "pest control agent" indicates a substance that serves to repel or attract pests, to decrease, inhibit or promote their growth, development or their activity. Pests refer to any living organism, whether animal, plant or fungus, which is invasive or troublesome to plants or animals, pests include insects notably arthropods, mites, spiders, fungi, weeds, bacteria and other microorganisms.

According to a particular embodiment, the hydrophobic material is free of any active ingredient (such as perfume). According to this particular embodiment, it comprises, preferably consists of hydrophobic solvents, preferably chosen in the group consisting of isopropyl myristate, tryglycerides (e.g. Neobee® MCT oil, vegetable oils), D-limonene, silicone oil, mineral oil, and mixtures thereof with optionally hydrophilic solvents preferably chosen in the group consisting of 1,4-butanediol, benzyl alcohol, triethyl citrate, triacetin, benzyl acetate, ethyl acetate, propylene glycol (1,2-propanediol), 1,3-propanediol, dipropylene glycol, glycerol, glycol ethers and mixtures thereof.

According to any one of the invention's embodiments, the hydrophobic material represents between about 10% and 60% w/w, or even between 15% and 45% w/w, by weight, relative to the total weight of the oil phase.

According to a particular embodiment, the oil phase essentially consists of the polyfunctional monomer and a perfume or flavor oil.

Polymeric Shell

According to an embodiment, the polymeric shell comprises (or is made of) a material selected from the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof.

According to a particular embodiment, the material is polyurea and/or polyurethane.

According to an embodiment, the polymeric material is present in an amount less than 20% by weight based on the total weight of the microcapsule.

According to another embodiment, the polymeric material is present in an amount less than 10% by weight based on the total weight of the microcapsule.

According to another embodiment, the polymeric material is present in an amount less than 6% by weight based on the total weight of the microcapsule.

According to an embodiment, the polymeric material is present in an amount less than 12% by weight based on the total weight of the microcapsule slurry.

According to another embodiment, the polymeric material is present in an amount less than 6% by weight based on the total weight of the microcapsule slurry.

According to another embodiment, the polymeric material is present in an amount less than 3% by weight based on the total weight of the microcapsule slurry.

Indeed, it has been underlined that even with a reduced amount of the polymeric material forming the shell, microcapsules still show good stability in consumer products.

Chitosan Particles

According to the invention, chitosan comprised in the shell are solid particles.

According to an embodiment, the chitosan particles are embedded within the shell.

According to an embodiment, the solid particles can be dispersed in water to form a homogeneous suspension of particles.

Preferred chitosan particles are those having an average diameter of at most 5 μm, more preferably of at most 3 μm.

The relative ratio of chitosan particles, relative to the hydrophobic material may be comprised between 1:1 and 1:300, preferably between 1:1 and 1:100.

Chitosan particles are comprised within the polymeric shell, meaning that they preferably participate to the polymeric shell formation and have covalent bond interactions with the polymeric shell, or incorporate into the polymeric shell or/and adhere to the polymeric shell under non-covalent interactions.

According to a particular embodiment, the chitosan particles are cross-linked chitosan particles. Chitosan particles are preferably cross-linked with a cross-linker chosen in the group consisting of water soluble inorganic polyanion, water soluble di-aldehydes or poly-aldehydes, and mixtures thereof. Water soluble inorganic polyanions may include phosphate based, silicate based, sulfate based, borate based salts and mixtures thereof.

According to a particular embodiment, the cross-linker is chosen in the group consisting of sodium triphosphate, sodium hexametaphoshpate, trisodium trimetaphosphate, sodium pyrophosphate, sodium phosphate and mixtures thereof. More particularly, the cross-linker is sodium triphosphate.

According to an embodiment, the weight ratio between chitosan polymer (i.e chitosan) and the cross-linker in the cross-linked chitosan particles is between 50:1 and 1:20, particularly between 50:1 and 1:10, more particularly between 20:1 and 1:1.

According to a particular embodiment, the core-shell microcapsule comprises:
a) an oil-based core comprising a perfume oil; and
b) a polyurea-based shell comprising cross-linked chitosan particles, wherein chitosan particles are preferably cross-linked with phosphate based salt, preferably sodium triphosphate.

According to an embodiment, the cross-linked chitosan particles are embedded within the polyurea-shell.

Optional Components

When microcapsules are in the form of a slurry, the microcapsule slurry comprising auxiliary ingredients selected from the group of thickening agents/rheology modifiers, antimicrobial agents, opacity-building agents, mica particles, salt, pH stabilizers/buffering ingredients, preferably in an amount comprised between 0 and 15% by weight based on the total weight of the slurry.

According to another embodiment, the microcapsule slurry of the invention comprises additional free (i.e non-encapsulated) perfume, preferably in an amount comprised between 5 and 50% by weight based on the total weight of the slurry.

Optional Outer Coating

According to a particular embodiment of the invention, microcapsules according to the invention comprise an outer coating material selected from the group consisting of a polysaccharide, a cationic polymer and mixtures thereof to form an outer coating to the microcapsule.

Polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose, pectin and mixtures thereof.

According to a particular embodiment, the coating consists of a cationic coating.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

According to any one of the above embodiments of the invention, there is added an amount of polymer described above comprised between about 0% and 5% w/w, or even between about 0.1% and 2% w/w, percentage being expressed on a w/w basis relative to the total weight of the slurry. It is clearly understood by a person skilled in the art that only part of said added polymers will be incorporated into/deposited on the microcapsule shell.

Process for Preparing Core-Shell Microcapsule

Core-shell microcapsules of the invention can be prepared according different processes depending notably on the nature of the polymeric wall.

Another object of the invention is a process for preparing core-shell microcapsules as defined above, wherein the process comprises the steps of:
1) suspending in water chitosan particles to form a water phase;
2) preparing an oil phase comprising a hydrophobic material, preferably a perfume oil;
3) adding the oil phase to the water phase and mixing them to form an oil-in-water Pickering emulsion, under conditions allowing the formation of core-shell microcapsule by interfacial polymerization and/or interfacial reaction, wherein a polyfunctional monomer is added in step 1) in the water phase and/or in step 2) in the oil phase.

According to an embodiment, in step 3), the oil phase is added into the water phase under conditions allowing the reaction of polyfunctional monomer to form polymeric shell at oil-water interface in the presence of chitosan particles.

According to a particular embodiment, the interfacial polymerization and/or interfacial reaction takes place between the polyfunctional monomer and chitosan particles.

According to this embodiment, the shell is formed via the reaction between the polyfunctional monomer in oil, with water and chitosan at oil-in-water interface.

According to an embodiment, the polyfunctional monomer is added in the oil phase in step 2).

The previous embodiment is particularly suitable, when the polyfunctional monomer is soluble in oil (for example when polyisocyanate is used as a polyfunctional monomer).

According to an embodiment, the polyfunctional monomer is added in the water phase in step 1).

The previous embodiment is particularly suitable, when the polyfunctional monomer is soluble in water (for example when a melamine resin is used as a polyfunctional monomer).

According to an embodiment, a first polyfunctional monomer is added in the water phase in step 1) (for example a melanin resin) and a second polyfunctional monomer (for example a polyisocyanate) is added in the oil phase in step 2).

According to a particular embodiment, the process of the invention comprises the step of adding a polymeric emulsifier in step 1) in the water phase.

By "polymeric emulsifier", it meant an emulsifier having both a polar group with an affinity for water (hydrophilic) and a nonpolar group with an affinity for oil (lipophilic). The hydrophilic part will dissolve in the water phase and the hydrophobic part will dissolve in the oil phase providing a film around droplets. Chitosan particles used in the present invention are not polymeric emulsifier. Chitosan particles belong to colloidal particle stabilizer.

This optional polymeric emulsifier allows assisting to stabilize the oil droplets in the presence of chitosan particles. This embodiment can be particularly suitable when chitosan particles concentration is low. The polymeric emulsifier can be an ionic or non-ionic surfactant. As non-limiting examples, non-ionic polymers include polyvinyl alcohol, cellulose derivatives such hydroxyethyl cellulose, polyethylene oxide, co-polymers of polyethylene oxide and polyethylene or polypropylene oxide, co-polymers alkyl acrylates and N-vinypyrrolidone, and non-ionic polysaccharide. Ionic polymers include co-polymers of acrylamide and acrylic acid, acid anionic surfactant (such as sodium dodecyl sulfate), acrylic co-polymers bearing a sulfonate group, and co-polymers of vinyl ethers and maleic anhydride, and ionic polysaccharide.

According to an embodiment, during the process, no polymeric emulsifier is added at any stage of the process.

According to a particular embodiment, the process of the invention comprises the step of adding a colloidal stabilizer or colloidal particle stabilizer (in addition to the chitosan particles), in step 1), in the water phase.

According to a particular embodiment, the process of the invention comprises the step of adding a reactant in step 1) and/or step 3). This optional reactant can participate to the shell formation of microcapsules. The reactant can be water soluble or water suspensible. Examples of suitable reactant include alcohols, amines, phenols, thiols, (meth)acrylates, epoxides, anhydrides with two or more functionalities, polyalkoxysilane, melamine-formaldehyde resin and melamine-glyoxal resin, and mixtures thereof.

When a reactant is added, the reactant can also react with the polyfunctional monomer for polymeric shell formation. According to this embodiment, in addition to the reactant, the chitosan particles also participate to the polymeric shell formation.

FIG. 1 schematises the formation of a Pickering emulsion when chitosan particles or cross-linked chitosan particles are used. According to a particular embodiment, the microcapsules according to the invention are prepared in the absence of any molecular surfactant (also called polymeric emulsifier).

In the first step of the process, the chitosan particles are dispersed in an aqueous phase.

Typically, this is done using high mechanical agitation.

When chitosan particles are not cross-linked, said particles may be obtained by:
(i) dissolving chitosan into water under acid conditions, typically at a pH between 3 and 5; and
(ii) increasing the pH to form chitosan particles, typically at a pH greater than 6.5.

When chitosan particles are cross-linked, said particles may be obtained by:
(i) dissolving chitosan into water under acid conditions, typically at a pH between 3 and 5; and
(ii) adding a cross-linker into chitosan solution of step (i) to form cross-linked chitosan particles,
(iii) optionally, adjusting the pH between 5 and 7.

Typically, step (ii) consists of mixing the cross-linker and chitosan solution obtained in step (i) during stirring or agitation.

According to an embodiment, the total amount of chitosan particles present in water phase is comprised between 0.01 and 10 wt %, preferably between 0.1 and 5 wt % based on the total weight of the water phase.

According to an embodiment, in a second step, at least one oil soluble polyfunctional monomer is dissolved in a hydrophobic material (for example, a perfume or flavour oil) to form an oil phase, which is then added to the water phase to form a Pickering emulsion, the mean droplet size of which is comprised between 1 and 3000 microns, preferably between 1 and 500 microns, more preferably between 5 and 50 microns. The oil-in-water Pickering emulsion is made for instance by using high speed mechanical disperser or ultrasonic dispersers at room temperature.

According to an embodiment, the oil phase represents between 5 and 60%, preferably between 20 and 40% of the Pickering emulsion.

Once the Pickering emulsion is formed, the pH value is preferably maintained at 5-6, or adjusted to a value above 6.5, or adjusted to a value above 8.5 and preferably not higher than 11. However, this step can be omitted.

The interfacial polymerization and/or interfacial reaction can be carried out typically at a temperature between 50° C. and 90° C. under stirring for 2 to 40 hours to complete the reaction and form hybrid microcapsules in the form of a slurry. However, the heating step can be omitted.

According to an embodiment, the polyfunctional monomer is chosen in the group consisting of at least one polyisocyanate, poly maleic anhydride, poly acid chloride, polyepoxide, acrylate monomers, polyalkoxysilane, melamine-based resin and mixtures thereof.

According to a particular embodiment, the monomer added in step 2) is at least one polyisocyanate having at least two isocyanate functional groups.

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90. According to an embodiment, the polyisocyanate used in the process of the invention is present in amounts representing from 0.1 and 15%, preferably from 0.5 and 5% by weight based on the total amount of the oil phase.

Optional Step: Optional Outer Coating

According to a particular embodiment of the invention, at the end of step 3) or during step 3), one may also add to the invention's slurry a polymer selected from the group consisting of a non-ionic polysaccharide, a cationic polymer and mixtures thereof to form an outer coating to the microcapsule. Non-ionic polysaccharide and cationic polymer are defined as previously.

Process for Preparing Microcapsule Powder

Another object of the invention is a process for preparing a microcapsule powder comprising the steps as defined above and an additional step consisting of submitting the slurry obtained in step 3) to a drying process, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, vegetable gums, pectins, xanthans, alginates, carragenans or cellulose derivatives to provide microcapsules in a powder form.

However, one may cite also other drying method such as the extrusion, plating, spray granulation, the fluidized bed, or even a drying at room temperature using materials (carrier, desiccant) that meet specific criteria as disclosed in WO2017/134179.

According to a particular embodiment, the carrier material contains free perfume oil which can be the same or different from the perfume from the core of the microcapsules.

Core-Shell Microcapsule

Another object of the invention is a microcapsule obtainable by the process as described above.

Perfuming Composition and Consumer Products

The microcapsules of the invention can be used in combination with active ingredients. An object of the invention is therefore a composition comprising:
  (i) microcapsules as defined above;
  (ii) an active ingredient, preferably chosen in the group consisting of a cosmetic ingredient, skin caring ingredient, perfume ingredient, flavor ingredient, malodour counteracting ingredient, bactericide ingredient, fungicide ingredient, pharmaceutical or agrochemical ingredient, a sanitizing ingredient, an insect repellent or attractant, and mixtures thereof.

The capsules of the invention show a good performance in terms of stability in challenging medium.

Another object of the present invention is a perfuming composition comprising:
  (i) microcapsules as defined above, wherein the oil comprises a perfume;
  (ii) at least one ingredient selected from the group consisting of a perfumery carrier, a perfumery co-ingredient and mixtures thereof;
  (iii) optionally at least one perfumery adjuvant.

As liquid perfumery carriers one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to at least impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.01 and 30% by weight of microcapsules as defined above.

The invention's microcapsules can advantageously be used in many application fields and used in consumer products. Microcapsules can be used in liquid form applicable to liquid consumer products as well as in powder form, applicable to powder consumer products.

According to a particular embodiment, the consumer product as defined above is liquid and comprises:
 a) from 2 to 65% by weight, relative to the total weight of the consumer product, of at least one surfactant;
 b) water or a water-miscible hydrophilic organic solvent; and
 c) a microcapsule slurry as defined above,
 d) optionally non-encapsulated perfume.

According to a particular embodiment, the consumer product as defined above is in a powder form and comprises:
 a) from 2 to 65% by weight, relative to the total weight of the consumer product, of at least one surfactant;
 b) a microcapsule powder as defined above.
 c) optionally perfume powder that is different from the microcapsules defined above.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care, surface care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsules than those here-disclosed.

In particular a liquid consumer product comprising:
 a) from 2 to 65% by weight, relative to the total weight of the consumer product, of at least one surfactant;
 b) water or a water-miscible hydrophilic organic solvent; and
 c) a perfuming composition as defined above is another object of the invention.

Also a powder consumer product comprising
 (a) from 2 to 65% by weight, relative to the total weight of the consumer product, of at least one surfactant; and
 (b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc.). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumed consumer products can be a perfume, such as a fine perfume, a cologne, an after-shave lotion, a body-splash; a fabric care product, such as a liquid or solid detergent, tablets and pods, a fabric softener, a dryer sheet, a fabric refresher, an ironing water, or a bleach; a personal-care product, such as a hair-care product (e.g. a shampoo, hair conditioner, a coloring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.); a hygiene product such as sanitary napkins, diapers, toilet paper.

Another object of the invention is a consumer product comprising:
 a personal care active base, and
 microcapsules as defined above or the perfuming composition as defined above,
 wherein the consumer product is in the form of a personal care composition.

Personal care active bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

The personal care composition is preferably chosen in the group consisting of a hair-care product (e.g. a shampoo, hair conditioner, a coloring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); Another object of the invention is a consumer product comprising:
- a home care or a fabric care active base, and
- microcapsules as defined above or the perfuming composition as defined above, wherein the consumer product is in the form of a home care or a fabric care composition.

Home care or fabric care active bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Preferably, the consumer product comprises from 0.1 to 15 wt %, more preferably between 0.2 and 5 wt % of the microcapsules of the present invention, these percentages being defined by weight relative to the total weight of the consumer product. Of course the above concentrations may be adapted according to the benefit effect desired in each product.

Fabric Softener

An object of the invention is a consumer product in the form of a fabric softener composition comprising:
- a fabric softener active base; preferably chosen in the group consisting of dialkyl quaternary ammonium salts, dialkyl ester quaternary ammonium salts (esterquats), Hamburg esterquat (HEQ), TEAQ (triethanolamine quat), silicones and mixtures thereof, preferably in an amount comprised between 85 and 99.95% by weight based on the total weight of the composition,
- microcapsules as defined above, preferably in an amount comprised between 0.05 to 15 wt %, more preferably between 0.1 and 5 wt % by weight based on the total weight of the composition.

Liquid Detergent

An object of the invention is a consumer product in the form of a liquid detergent composition comprising:
- a liquid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and non-ionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, preferably in an amount comprised between 85 and 99.95% by weight based on the total weight of the composition,
- microcapsules as defined above, preferably in an amount comprised between 0.05 to 15 wt %, more preferably between 0.1 and 5 wt % by weight based on the total weight of the composition.

Solid Detergent

An object of the invention is a consumer product in the form of a solid detergent composition comprising:
- a solid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and non-ionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, preferably in an amount comprised between 85 and 99.95% by weight based on the total weight of the composition,
- microcapsules as defined above, preferably in an amount comprised between 0.05 to 15 wt %, more preferably between 0.1 and 5 wt % by weight based on the total weight of the composition.

Shampoo/Shower Gel

An object of the invention is a consumer product in the form of a shampoo or a shower gel composition comprising:
- a shampoo or a shower gel active base; preferably chosen in the group consisting of sodium alkylether sulfate, ammonium alkylether sulfates, alkylamphoacetate, cocamidopropyl betaine, cocamide MEA, alkylglucosides and aminoacid based surfactants and mixtures thereof, preferably in an amount comprised between 85 and 99.95% by weight based on the total weight of the composition,
- microcapsules as defined above, preferably in an amount comprised between 0.05 to 15 wt %, more preferably between 0.1 and 5 wt % by weight based on the total weight of the composition.

Rinse-Off Conditioner

An object of the invention is a consumer product in the form of a rinse-off conditioner composition comprising:
- a rinse-off conditioner active base; preferably chosen in the group consisting of cetyltrimonium chloride, stearyl trimonium chloride, benzalkonium chloride, behentrimonium chloride and mixture thereof, preferably in an amount comprised between 85 and 99.95% by weight based on the total weight of the composition,
- microcapsules as defined above, preferably in an amount comprised between 0.05 to 15 wt %, more preferably between 0.1 and 5 wt % by weight based on the total weight of the composition.

Hair Coloration

An object of the invention is a consumer product in the form of an oxidative hair coloring composition comprising:
- an oxidizing phase comprising an oxidizing agent and an alkaline phase comprising an alkakine agent, a dye precursor and a coupling compound; wherein said dye precursor and said coupling compound form an oxidative hair dye in the presence of the oxidizing agent, preferably in an amount comprised between 85 and 99.95% by weight based on the total weight of the composition,
- microcapsules as defined above, preferably in an amount comprised between 0.05 to 15 wt %, more preferably between 0.1 and 5 wt % by weight based on the total weight of the composition.

By "oxidative hair coloring composition", it is meant a composition comprising two groups of colorless dye molecules: the dye precursor and the coupling agent. Upon reaction with each other through an oxidation process, they form a wide range of colored molecules (dyes) that are then trapped into the hair due their size. In other words, the dye precursor and the coupling compound form an oxidative hair dye in the presence of the oxidizing agent.

"Dye precursor" and "oxidative dye precursor" are used indifferently in the present invention.

Dye precursors can be aromatic compounds derived from benzene substituted by at least two electron donor groups such as $NH_2$ and OH in para or ortho positions to confer the property of easy oxidation.

According to an embodiment, dye precursors are chosen in the group consisting of p-phenylene diamine, 2,5-diamino toluene, N,N-bis(2-hydroxymethyl)-p-phenylene diamine, 4-aminophenol, 1,4-diamino-benzene, and mixtures thereof.

The primary dye precursors is used in combination with coupling agents. Coupling agents are preferably aromatic compounds derived from benzene and substituted by groups such as $NH_2$ and OH in the meta position and do not produce color singly, but which modify the color, shade or intensity of the colors developed by the dye precursor.

According to an embodiment, the coupling agent is chosen in the group consisting of resorcinol, 2-methyl resorcinol, 4-chlororesorchinol, 2,5-diamino-toluene, 1,3-diamino-benzene, 2,4-diaminophenoxyethanol HCl, 2-amino-hydroxyethylaminoanisole sulfate, 4-amino-2-hydroxytoluene, and mixtures thereof.

The oxidative dye precursor is preferably used in an amount comprised between 0.001% and 5%, preferably between 0.1% and 4% by weight based on the total weight of the composition.

The use of oxidative dye precursors and coupling agents in hair coloring formulation have been widely disclosed in the prior art and is well-known from the person skilled in the art. One may cite for example EP0946133A1, the content of which is incorporated by reference.

The alkaline phase comprises an alkaline agent, preferably chosen in the group consisting of ammonia hydroxide, ammonia carbonate, ethanolamine, potassium hydroxide, sodium borate, sodium carbonate, triethanolamine and mixtures thereof.

The alkaline agent is preferably used in an amount comprised between 1% and 10%, preferably between 3% and 9% by weight based on the total weight of the composition.

According to the invention, the coupling agent and the dye precursor in an alkaline medium form an oxidative hair dye in the presence of the oxidizing agent.

The oxidizing agent will supply the necessary oxygen gas to develop color molecules and create a change in hair color. The oxidizing agent should be safe and effective for use in the compositions herein.

Preferably, the oxidizing agents suitable for use herein will be soluble in the compositions according to the present invention when in liquid form and/or in the form intended to be used.

Preferably, oxidizing agents suitable for use herein will be water-soluble. Suitable oxidizing agents for use herein are selected from inorganic peroxygen oxidizing agents, preformed organic peroxyacid oxidizing agents and organic peroxide oxidizing agents or mixtures thereof.

The oxidizing agent is preferably used in an amount comprised between 5 and 30%, preferably between 5 and 25% by weight based on the total weight of the composition.

Components commonly used in cosmetic compositions may be added into the hair coloring composition as defined in the present invention. One may cite for example, surfactants, cationic polymers, oily substances, silicone derivatives, free perfume, preservatives, ultraviolet absorbents, antioxidants, germicides, propellants, thickeners.

According to a particular embodiment, the hair coloring composition comprises one or more quaternary ammonium compounds, preferably chosen in the group consisting of cetyltrimonium chloride, stearyl trimonium chloride, benzalkonium chloride, behentrimonium chloride and mixture thereof to confer hair conditioner benefits.

Perfuming Composition

According to a particular embodiment, the consumer product is in the form of a perfuming composition comprising:

0.1 to 30%, preferably 0.1 to 20% of microcapsules as defined previously, 0 to 40%, preferably 3-40% of perfume, and 20-90, preferably 40-90% of ethanol, by weight based on the total weight of the perfuming composition.

The invention will now be further described by way of examples. It will be appreciated that the invention as claimed is not intended to be limited in any way by these examples.

EXAMPLES

Example 1

Microcapsules Preparation

Microcapsules were prepared according to the general protocol described below.

Chitosan polymer is firstly dissolved into acetic acid solution under stirring, and chitosan polymer is optionally cross-linked by adding sodium tripolyphosphate solution to form particles under stirring at specific pH 4 value and the pH of the suspension is increased at a pH 6 to form particles in an aqueous phase.

Then, an oil phase (including for example a polyisocyanate) is mixed with the aqueous phase, wherein the oil phase and/or the water phase comprises a polyfunctional monomer. A Pickering emulsion is made by using a homogenizer, Ultra Turrax, IKA T25, at 24 000 rpm for 5 min. The formulation is described in Tables 1-11 below.

In another step, interfacial reaction is carried out at 80° C. under stirring for 3 hours.

The obtained microcapsules are in the form of a slurry (suspension in water).

TABLE 1

Formulation of the perfume oil

| Ingredients | % in oil |
|---|---|
| Ethyl 2-methyl-pentanoate | 3.20% |
| Eucalyptol | 7.80% |
| 2,4-Dimethyl-3-cyclohexene-1-carbaldehyde | 0.75% |
| Aldehyde C10 | 0.75% |
| Citronellyl Nitrile | 4.30% |
| Isobornyl acetate | 3.00% |
| 2-tert-butyl-1-cyclohexyl acetate | 9.80% |
| Citronellyl Acetate | 1.30% |
| 2-Methylundecanal | 3.00% |
| Diphenyloxide | 0.80% |
| Aldehyde C12 | 1.30% |
| Dicyclopentadiene acetate | 9.85% |
| Ionone beta | 3.30% |
| Undecalactone gamma | 18.75% |
| Hexyl Salicylate | 15.90% |
| Benzyl Salicylate | 16.20% |

TABLE 2

Formulation of microcapsules A preparation

| Ingredient | % wt |
| --- | --- |
| Chitosan[1] | 0.7 |
| Deionized water | 68.49 |
| Acetic acid | 0.69 |
| Trimethylol propane-adduct of xylylene diisocyanate [2] | 0.6 |
| Sodium tripolyphosphate | 0.12 |
| Perfume oil[3] | 29.4 |

[1] Origin: Shanghai Aladdin Bio-Chem Technology Co., LTD, China
[2] Takenate ® D-110 N (74.4% solid content), trademark and origin from Mitsui
[3] see table 1

TABLE 3

Formulation of microcapsules B preparation

| Ingredient | % wt |
| --- | --- |
| Chitosan[1] | 0.5 |
| Deionized water | 66.74 |
| Acetic acid | 0.68 |
| Trimethylol propane-adduct of xylylene diisocyanate [2] | 0.6 |
| Sodium tripolyphosphate | 0.08 |
| Perfume oil[3] | 29.4 |

[1] Origin: Shanghai Aladdin Bio-Chem Technology Co., LTD, China
[2] Takenate ® D-110 N (74.4% solid content), trademark and origin from Mitsui
[3] see table 1

TABLE 4

Formulation of microcapsules C preparation

| Ingredient | % wt |
| --- | --- |
| Chitosan[1] | 0.35 |
| Deionized water | 68.89 |
| Acetic acid | 0.7 |
| Trimethylol propane-adduct of xylylene diisocyanate [2] | 0.6 |
| Sodium tripolyphosphate | 0.006 |
| Perfume oil[3] | 29.4 |

[1] Origin: Shanghai Aladdin Bio-Chem Technology Co., LTD, China
[2] Takenate ® D-110 N (74.4% solid content), trademark and origin from Mitsui
[3] see table 1

TABLE 5

Formulation of microcapsules D preparation

| Ingredient | % wt |
| --- | --- |
| Chitosan[1] | 0.14 |
| Deionized water | 69.15 |
| Acetic acid | 0.7 |
| Trimethylol propane-adduct of xylylene diisocyanate [2] | 0.6 |
| Sodium tripolyphosphate | 0.014 |
| Perfume oil[3] | 29.4 |

[1] Origin: Shanghai Aladdin Bio-Chem Technology Co., LTD, China
[2] Takenate ® D-110 N (74.4% solid content), trademark and origin from Mitsui
[3] see table 1

TABLE 6

Formulation of microcapsules E preparation

| Ingredient | % wt |
| --- | --- |
| Chitosan[1] | 0.5 |
| Deionized water | 66.74 |
| Acetic acid | 0.68 |
| Trimethylol propane-adduct of xylylene diisocyanate [2] | 0.45 |
| Sodium tripolyphosphate | 0.08 |
| Perfume oil[3] | 29.55 |

[1] Origin: Shanghai Aladdin Bio-Chem Technology Co., LTD, China
[2] Takenate ® D-110 N (74.4% solid content), trademark and origin from Mitsui
[3] see table 1

TABLE 7

Formulation of microcapsules F preparation

| Ingredient | % wt |
| --- | --- |
| Chitosan[1] | 0.7 |
| Deionized water | 68.61 |
| Trimethylol propane-adduct of xylylene diisocyanate [2] | 0.6 |
| Acetic acid | 0.69 |
| Perfume oil[3] | 29.4 |

[1] Origin: Shanghai Aladdin Bio-Chem Technology Co., LTD, China
[2] Takenate ® D-110 N (74.4% solid content), trademark and origin from Mitsui
[3] see table 1

TABLE 8

Formulation of microcapsules G preparation

| Ingredient | % wt |
| --- | --- |
| Chitosan[1] | 1.05 |
| Deionized water | 68.26 |
| Trimethylol propane-adduct of xylylene diisocyanate [2] | 0.6 |
| Acetic acid | 0.69 |
| Perfume oil[3] | 29.4 |

[1] Origin: Shanghai Aladdin Bio-Chem Technology Co., LTD, China
[2] Takenate ® D-110 N (74.4% solid content), trademark and origin from Mitsui
[3] see table 1

TABLE 9

Formulation of microcapsules H preparation

| Ingredient | % wt |
|---|---|
| Chitosan[1] | 0.7 |
| Deionized water | 68.48 |
| Acetic acid | 0.7 |
| Trimethylol propane-adduct of xylylene diisocyanate [2] | 0.3 |
| Biuret of hexamethylene diisocyanate [3] | 0.3 |
| Sodium tripolyphosphate | 0.12 |
| Perfume oil [4] | 29.4 |

[1] Origin: Shanghai Aladdin Bio-Chem Technology Co., LTD, China
[2] Takenate ® D-110 N (74.4% solid content), trademark and origin from Mitsui
[3] Desmodur ® N-100, trademark and origin from Covestro
[4] see table 1

TABLE 10

Formulation of microcapsules I preparation

| Ingredient | % wt |
|---|---|
| Chitosan[1] | 0.7 |
| Deionized water | 68.33 |
| Acetic acid | 0.7 |
| Butyl methacrylate | 2.0 |
| 1,4-Butanediol dimethacrylate | 2.8 |
| Sodium tripolyphosphate | 0.12 |
| Ammonium persulfate | 0.15 |
| Benzoyl peroxide | 0.15 |
| Perfume oil [2] | 25.05 |

[1] Origin: Shanghai Aladdin Bio-Chem Technology Co., LTD, China
[2] see table 1

TABLE 11

Formulation of microcapsules J preparation

| Ingredient | % wt |
|---|---|
| Chitosan[1] | 0.7 |
| Deionized water | 65.20 |
| Acetic acid | 0.68 |
| Trimethylol propane-adduct of xylylene diisocyanate [2] | 0.6 |
| Melamine-glyoxal resin [3] | 2.3 |
| Sodium tripolyphosphate | 0.12 |
| Cationic acrylic copolymer [4] | 1.0 |
| Perfume oil [5] | 29.55 |

[1] Origin: Shanghai Aladdin Bio-Chem Technology Co., LTD, China
[2] Takenate ® D-110 N (74.4% solid content), trademark and origin from Mitsui
[3] Reaction of Melamine, Glyoxal and 2,2-Dimethoxyacetaldehyde
[4] Salcare ® SC 60, trademark and origin from BASF
[5] see table 1

Mean size and zeta potential of prepared microcapsules were measured (see table 12).

The size distribution of the microcapsules was controlled by Optical Microscopy and Light Scattering (Mastersizer 3000, Malvern).

Zeta potential of the microcapsules was determined by using a Zetasizer Nano ZS (Malvern Instruments.

TABLE 12

Mean size and zeta potential of microcapsules

| Microcapsules | Mean Size d(v, 0.5) | Zeta Potential |
|---|---|---|
| A | 27 μm | 18.7 mV |
| B | 32 μm | 15.5 mV |
| C | 16 μm | 12.1 mV |
| D | 28 μm | 16.5 mV |
| E | 35 μm | 18.1 mV |
| F | 31 μm | 6.1 mV |
| G | 18 μm | 9.0 mV |
| H | 31 μm | 18.8 mV |
| I | 43 μm | 26.5 mV |
| J | 47 μm | 28.2 mV |

Example 2

Storage Stability in a Fabric Softener Composition

The storage stability of the capsules in fabric softener was evaluated. Microcapsules slurry of the present invention was diluted in the fabric softener composition described in Table 13 at a dosage of 0.2%. The softener was stored during one month at 37° C. The amount of perfume having leaked out of the capsules was then measured by solvent extraction and GC-FID analysis (Table 14).

TABLE 13

Fabric softener composition

| Product | Origin | Wt % |
|---|---|---|
| Stepantex VL 90A | | 8.88 |
| Calcium Chloride Sol. 10% | | 0.36 |
| Proxel GXL | Avecia | 0.04 |
| Perfume | Firmenich SA | 1 |
| Water | | 89.72 |
| TOTAL | | 100 |

TABLE 14

Oil leakage measurement

| Capsules | Leakage 30 days (%) |
|---|---|
| A | 19 |
| B | 22 |
| C | 42 |
| D | 21 |
| E | 27 |
| F | 30 |
| G | 33 |
| H | 31 |
| J | 14 |

One can conclude from Table 14 that microcapsules of the present invention show good stability in challenging bases despite the low amount of polyfunctional monomer in the shell.

Example 3

Olfactive Performance of the Microcapsules

The slurry of microcapsules is diluted in softener base at 0.11% of free perfume. The sample is agitated in the turbulat at 41 rpm for 5 minutes. To get closer to the dilution in the washing machine during the rinsing cycle, the sample is diluted at 2% in deionized water. 1 mL of this solution is withdrawn and deposited on the blotter. The sample is let drying 24h at RT before processing to the evaluation before and after rubbing.

Evaluation scale: (fragrance intensity): 1=no fragrance odor; 2=just detectable; 3=weak; 4=moderate; 5=slightly strong; 6=intense; 7=very intense.

TABLE 15

Sensory analysis result of microcapsule diluted in fabric softener and applied on blotter

| Microcapsules | Before rubbing | After rubbing |
| --- | --- | --- |
| A | 2.4 | 5.2 |
| B | 2.8 | 5.8 |
| C | 2.6 | 5.0 |
| D | 2.3 | 5.5 |
| E | 2.8 | 4.8 |
| F | 2.2 | 4.3 |
| G | 2.4 | 4.4 |
| H | 2.6 | 5.1 |
| I | 2.9 | 4.8 |
| J | 2.1 | 5.6 |

Microcapsules show a good rubbing effect, confirming the efficient encapsulation.

Example 4

Liquid Detergent Composition

Microcapsules A-G of the present invention are dispersed in a liquid detergent base described in Table 16 to obtain a concentration of encapsulated perfume oil at 0.22%.

TABLE 16

Liquid detergent composition

| Ingredients | Concentration [wt %] |
| --- | --- |
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Protease | 0.2 |
| Amylase | 0.2 |
| Mannanase | 0.2 |
| Acrylates/Steareth-20 Methacrylate structuring Crosspolymer[4] | 6 |
| Deionized Water | 27.4 |

[1] Hostapur SAS 60; Origin: Clariant
[2] Edenor K 12-18; Origin: Cognis
[3] Genapol LA 070; Origin: Clariant
[4] Aculyn 88; Origin: Dow Chemical Example 5

Rinse-Off Conditioner

Microcapsules A-G of the present invention are dispersed in a rinse-off conditioner base described in table 17 to obtain a concentration of encapsulated perfume oil at 0.5%.

TABLE 17

Rinse-off conditioner composition

| | Ingredients | Concentration [wt %] |
| --- | --- | --- |
| A | Water deionized | 81.8 |
| | Behentrimonium Chloride [1] | 2.5 |
| | Hydroxyethylcellulose [2] | 1.5 |
| B | Cetearyl Alcohol [3] | 4 |
| | Glyceryl Stearate (and) PEG-100 Stearate [4] | 2 |
| | Behentrimonium Methosulfate (and) Cetyl alcohol (and) Butylene Glycol [5] | 4 |
| | Ethoxy (20) Stearyl Alcohol [6] | 1 |
| C | Amodimethicone (and) Trideceth-12 (and) Cetrimonium Chloride [7] | 3 |
| | Chlorhexidine Digluconate [8] 20% aqueous solution | 0.2 |
| D | Citric acid 10% aqueous sol. till pH 3.5-4 | q.s. |
| | TOTAL: | 100 |

[1] Genamin KDM P, Clariant
[2] Tylose H10 Y G4, Shin Etsu
[3] Lanette O, BASF
[4] Arlacel 165-FP-MBAL-PA-(RB), Croda
[5] Incroquat Behenyl TMS-50-MBAL-PA-(MH) HA4112, Croda
[6] SP Brij S20 MBAL-PA(RB), Croda
[7] Xiameter DC MEM-0949 Emulsion, Dow Corning
[8] Alfa Aesar Example 6

Shampoo Composition

Microcapsules A-G of the present invention are weighed and mixed in a shampoo composition to add the equivalent of 0.2% perfume.

TABLE 18

Shampoo composition

| | Ingredients | Concentration [wt %] |
| --- | --- | --- |
| A | Water deionized | 44.4 |
| | Polyquaternium-10 [1] | 0.3 |
| | Glycerin 85% [2] | 1 |
| | DMDM Hydantoin [3] | 0.2 |
| B | Sodium Laureth Sulfate [4] | 28 |
| | Cocamidopropyl Betaine [5] | 3.2 |
| | Disodium Cocoamphodiacetate [6] | 4 |
| | Ethoxy (20) Stearyl Alcohol [6] | 1 |
| C | Sodium Laureth Sulfate [4] | 3 |
| | Glyceryl Laureate [7] | 0.2 |
| D | Water deionized | 1 |
| | Sodium Methylparaben [8] | 0.1 |
| E | Sodium Chloride 10% aqueous sol. | 15 |
| | Citric acid 10% aqueous sol. till pH 5.5-6 | q.s. |
| | Perfume | 0.5 |
| | TOTAL: | 100 |

[1] Ucare Polymer JR-400, Noveon
[2] Schweizerhall
[3] Glydant, Lonza
[4] Texapon NSO IS, Cognis
[5] Tego Betain F 50, Evonik
[6] Amphotensid GB 2009, Zschimmer & Schwarz
[7] Monomuls 90 L-12, Gruenau
[8] Nipagin Monosodium, NIPA

Example 7

Antiperspirant Roll-on Emulsion Composition

Microcapsules A-G of the present invention are weighed and mixed in antiperspirant roll-on emulsion composition to add the equivalent of 0.2% perfume.

TABLE 19

Antiperspirant composition

| Ingredient | Amount (wt %) |
|---|---|
| Steareth-2[1] (Part A) | 3.25 |
| Steareth-21[2] (Part A) | 0.75 |
| PPG-15 Stearyl Ether[3] (Part A) | 4 |
| WATER deionised (Part B) | 51 |
| Aluminum Chlorohydrate 50% aqueous solution[4] (Part C) | 40 |
| Fragrance (Part D) | 1 |

[1] BRIJ 72; origin: ICI
[2] BRIJ 721; origin: ICI
[3] ARLAMOL E; origin: UNIQEMA-CRODA
[4] LOCRON L; origin: CLARIAN Part A and B are heated separately to 75° C.; Part A is added to Part B under stirring and the mixture is homogenized for 10 min. Then, the mixture is cooled under stirring; and Part C is slowly added when the mixture reached 45° C. and Part D when the mixture reached at 35° C. while stirring. Then the mixture is cooled to room temperature.

Example 8

Shower-Gel Composition

Microcapsules A-G of the present invention are weighed and mixed in the following composition to add the equivalent of 0.2% perfume.

TABLE 20

Shower gel composition

| Ingredients | Amount (% wt) | Function |
|---|---|---|
| WATER deionised | 49.350 | Solvent |
| Tetrasodium EDTA [1] | 0.050 | Chelating agent |
| Acrylates Copolymer[2] | 6.000 | Thickener |
| Sodium C12-C15 Pareth Sulfate [3] | 35.000 | Surfactant |
| Sodium Hydroxide 20% aqueous solution | 1.000 | pH adjuster |
| Cocamidopropyl Betaine[4] | 8.000 | Surfactant |
| Methylchloroisothiazolinone and Methylisothiazolinone[5] | 0.100 | Preservative |
| Citric Acid (40%) | 0.500 | pH adjuster |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS

The invention claimed is:

1. A core-shell microcapsule comprising:
   a) an oil-based core comprising a hydrophobic material; and
   b) a polymeric shell comprising chitosan particles;
   wherein the chitosan particles are cross-linked chitosan particles.

2. The microcapsule according to claim 1, wherein the polymeric shell is made of a polymeric material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum arabic and mixtures thereof.

3. The microcapsule according to claim 2, wherein the polymeric shell is made of a material selected from the group consisting of polyurea, polyurethane and mixtures thereof.

4. The microcapsule according to claim 1, wherein the chitosan particles are cross-linked with a cross-linker selected from the group consisting of water soluble inorganic polyanion, water soluble di-aldehydes or poly-aldehydes, and mixtures thereof.

5. The microcapsule according to claim 4, wherein the cross-linker is selected from the group consisting of sodium triphosphate, sodium hexametaphoshpate, trisodium trimetaphosphate, sodium pyrophosphate, sodium phosphate and mixtures thereof.

6. The microcapsule according to claim 1, wherein the polymeric shell comprises less than 20% by weight of a polymeric material based on the total weight of the microcapsule.

7. The microcapsule according to claim 1, wherein:
   a) the oil-based core comprises a perfume oil; and
   b) the polymeric shell comprises a polyurea-based shell comprising cross-linked chitosan particles, wherein chitosan particles are cross-linked with phosphate based salt.

8. A process for preparing core-shell microcapsules as defined in claim 1, wherein the process comprises the steps of:
   1) suspending in water chitosan particles to form a water phase;
   2) preparing an oil phase comprising a hydrophobic material; and
   3) adding the oil phase to the water phase and mixing them to form an oil-in-water Pickering emulsion, under conditions allowing the formation of core-shell microcapsule by interfacial polymerization and/or interfacial reaction,
   wherein a polyfunctional monomer is added in step 1) in the water phase and/or in step 2) in the oil phase.

9. The process according to claim 8, wherein the polyfunctional monomer is selected from the group consisting of at least one polyisocyanate, poly maleic anhydride, poly acid chloride, polyepoxide, acrylate monomers, polyalkoxysilane, melamine-based resin and mixtures thereof.

10. The process according to claim 8, characterized in that chitosan particles are obtained by:
    (i) dissolving chitosan into water under acid conditions; and
    (ii) increasing the pH to form chitosan particles.

11. The process according to claim 8, characterized in that chitosan particles are cross-linked and are obtained by:
    (i) dissolving chitosan into water under acid conditions; and
    (ii) adding a cross-linker into chitosan solution of step (i) to form cross-linked chitosan particles.

12. The process according to claim 8, wherein the total amount of chitosan particles present in the water phase is comprised between 0.01 and 10 wt % based on the total weight of the water phase.

13. The process according to claim 8, wherein the oil phase represents between 5 and 60% of the Pickering emulsion.

14. A consumer product comprising:
a personal care active base, and
microcapsules as defined in claim 1,
wherein the consumer product is in the form of a personal care composition.

15. A consumer product comprising:
a home care or a fabric care active base, and
microcapsules as defined in claim 1,
wherein the consumer product is in the form of a home care or a fabric care composition.

16. The microcapsule according to claim 1, wherein the hydrophobic material comprises a perfume oil.

17. The microcapsule according to claim 7, wherein the chitosan particles are cross-linked with sodium triphosphate.

18. The process according to claim 12, wherein the total amount of chitosan particles present in the water phase is comprised between 0.1 and 5 wt % based on the total weight of the water phase.

19. The process according to claim 13, wherein the oil phase represents between 20 and 40% of the Pickering emulsion.

\* \* \* \* \*